US012733970B2

(12) United States Patent
Bates et al.

(10) Patent No.: US 12,733,970 B2
(45) Date of Patent: Sep. 15, 2026

(54) RF ABLATION SYSTEMS WITH A BIPOLAR RF ELECTRODE AND METHODS FOR MAKING AND USING

(71) Applicant: Boston Scientific Neuromodulation Corporation, Valencia, CA (US)

(72) Inventors: Gregory Bates, Bend, OR (US); Courtney Johnson, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 164 days.

(21) Appl. No.: 18/373,626

(22) Filed: Sep. 27, 2023

(65) Prior Publication Data

US 2024/0108394 A1 Apr. 4, 2024

Related U.S. Application Data

(60) Provisional application No. 63/413,133, filed on Oct. 4, 2022.

(51) Int. Cl.
*A61B 18/14* (2006.01)
*A61B 18/12* (2006.01)
*A61B 18/00* (2006.01)

(52) U.S. Cl.
CPC .................... *A61B 18/1206* (2013.01); *A61B 2018/00077* (2013.01); *A61B 2018/00083* (2013.01);

(Continued)

(58) Field of Classification Search
CPC ............ A61B 18/1206; A61B 18/1477; A61B 2018/00077; A61B 2018/00083;

(Continued)

(56) References Cited

U.S. PATENT DOCUMENTS 4,411,266 A 10/1983 Cosman
4,565,200 A 1/1986 Cosman (Continued)

FOREIGN PATENT DOCUMENTS

WO 99/40859 8/1999
WO 99/40860 8/1999

(Continued)

OTHER PUBLICATIONS

International Search Report and Written Opinion for PCT Application No. PCT/US2023/033835 mailed Feb. 26, 2024.

(Continued)

*Primary Examiner* — Michael F Peffley
(74) *Attorney, Agent, or Firm* — Branch Partners PLLC; Bruce E. Black

(57) ABSTRACT

An RF ablation system can include a bipolar RF electrode that has two electrodes. Some bipolar RF electrodes can include a metal tube forming one of the electrodes. The metal tube can have cuts to facilitate bending of the metal tube. Some bipolar RF electrodes can include a multi-lumen tube for the conductors. Some multi-lumen tubes can be made of a relatively high durometer material to provide column strength to the bipolar RF electrodes. Some RF ablation systems can include an adapter for a RF generator to connect each electrode to a different channel. A variety of arrangement of the channels of the RF generator and the conductors of the bipolar RF electrode can be used to couple the electrodes and a temperature sensor to the RF generator.

20 Claims, 3 Drawing Sheets

(52) U.S. Cl.
CPC ............... *A61B 2018/00577* (2013.01); *A61B 2018/126* (2013.01)

(58) Field of Classification Search
CPC .......... A61B 2018/00166; A61B 2018/00178; A61B 2018/0044; A61B 2018/00577; A61B 2018/00791; A61B 2018/126
See application file for complete search history.

(56) References Cited

U.S. PATENT DOCUMENTS 4,566,454 A 1/1986 Mehl et al.
4,597,379 A 7/1986 Kihn et al.
4,727,874 A 3/1988 Bowers et al.
4,807,620 A 2/1989 Strul et al.
5,360,009 A 11/1994 Herskovitz
5,433,739 A 7/1995 Sluijter et al.
5,571,147 A 11/1996 Sluijter et al.
5,728,143 A 3/1998 Gough et al.
5,769,847 A 6/1998 Panescu et al.
5,951,546 A 9/1999 Lorentzen
5,983,141 A 11/1999 Sluijter et al.
6,070,845 A 6/2000 Herskovitz
6,080,149 A 6/2000 Huang et al.
6,091,995 A 7/2000 Ingle et al.
6,104,959 A 8/2000 Spertell
6,161,048 A 12/2000 Sluijter et al.
6,203,524 B1 3/2001 Burney et al.
6,245,065 B1 6/2001 Panescu et al.
6,246,912 B1 6/2001 Sluijter et al.
6,259,952 B1 7/2001 Sluijter et al.
6,301,506 B1 10/2001 Den Boer et al.
6,321,120 B1 11/2001 Surbeck et al.
6,341,429 B1 1/2002 Herskovitz
6,397,106 B1 5/2002 DeBrouse
6,402,739 B1 6/2002 Neev
6,428,537 B1 8/2002 Swanson et al.
6,440,127 B2 8/2002 McGovern et al.
6,447,505 B2 9/2002 McGovern et al.
6,482,204 B1 11/2002 Lax et al.
6,517,534 B1 2/2003 McGovern et al.
6,530,922 B2 3/2003 Cosman et al.
6,692,493 B2 2/2004 McGovern et al.
6,699,242 B2 3/2004 Heggeness
6,743,226 B2 6/2004 Cosman et al.
6,843,789 B2 1/2005 Goble
6,853,864 B2 2/2005 Litovitz
6,869,430 B2 3/2005 Balbierz et al.
7,363,071 B2 4/2008 Damasco et al.
7,522,953 B2 4/2009 Kaula et al.
7,553,309 B2 6/2009 Buysse et al.
7,574,257 B2 8/2009 Rittman, III
7,725,155 B2 5/2010 Dowlatshahi
7,749,218 B2 7/2010 Pellegrino et al.
7,799,024 B2 9/2010 Randall
7,945,331 B2 5/2011 Vilims
8,123,782 B2 2/2012 Altarac et al.
8,128,662 B2 3/2012 Altarac et al.
8,273,108 B2 9/2012 Altarac et al.
8,277,488 B2 10/2012 Altarac et al.
8,292,922 B2 10/2012 Altarac et al.
8,361,067 B2 1/2013 Pellegrino et al.
8,361,607 B2 1/2013 Higuchi et al.
8,425,559 B2 4/2013 Altarac et al.
8,504,147 B2 8/2013 Deem et al.
8,512,333 B2 8/2013 Epstein et al.
8,518,037 B2 8/2013 Young
8,613,747 B2 12/2013 Altarac et al.
8,808,284 B2 8/2014 Pellegrino et al.
8,864,828 B2 10/2014 Altarac et al.
8,880,189 B2 11/2014 Lipani
8,945,183 B2 2/2015 Altarac et al.
8,979,830 B2 3/2015 Hennings
8,992,522 B2 3/2015 Pellegrino et al.
9,039,701 B2 5/2015 Pellegrino et al.
9,119,680 B2 9/2015 Altarac et al.
9,125,671 B2 * 9/2015 Germain ............ A61B 17/8811
9,155,570 B2 10/2015 Altarac et al.
9,155,572 B2 10/2015 Altarac et al.
9,161,783 B2 10/2015 Altarac et al.
9,173,676 B2 11/2015 Pellegrino et al.
9,186,186 B2 11/2015 Reglos et al.
9,393,055 B2 7/2016 Altarac et al.
9,532,812 B2 1/2017 Altarac et al.
9,572,603 B2 2/2017 Altarac et al.
9,717,552 B2 8/2017 Cosman et al.
9,861,398 B2 1/2018 Altarac et al.
9,949,782 B2 4/2018 Hagg et al.
9,956,011 B2 5/2018 Altarac et al.
9,956,032 B1 5/2018 Cosman et al.
10,080,587 B2 9/2018 Altarac et al.
10,111,703 B2 10/2018 Cosman, Jr. et al.
10,136,937 B1 11/2018 Cosman, Jr. et al.
10,136,942 B1 11/2018 Cosman, Jr. et al.
10,136,943 B1 11/2018 Cosman, Jr. et al.
10,166,047 B2 1/2019 Altarac et al.
10,194,971 B2 2/2019 Wegrzyn, III et al.
10,322,286 B2 6/2019 Viswanathan et al.
10,342,606 B2 7/2019 Cosman et al.
10,357,258 B2 7/2019 Patel et al.
10,363,063 B2 7/2019 Cosman
10,420,591 B2 9/2019 Snell et al.
10,448,959 B2 10/2019 Slobitker et al.
10,463,423 B2 11/2019 Sutton et al.
10,478,246 B2 11/2019 Pellegrino et al.
10,517,611 B2 12/2019 Patel et al.
10,548,654 B2 2/2020 Curley
10,588,687 B2 3/2020 Cosman, Jr. et al.
10,588,691 B2 * 3/2020 Pellegrino .......... A61B 18/1487
10,610,267 B2 4/2020 Altarac et al.
10,631,915 B1 4/2020 Cosman
10,639,098 B2 5/2020 Cosman et al.
10,639,101 B2 5/2020 Cosman et al.
10,653,456 B2 5/2020 Altarac et al.
10,709,502 B2 7/2020 Viswanathan
10,835,295 B2 11/2020 Altarac et al.
10,835,297 B2 11/2020 Altarac et al.
11,013,539 B2 5/2021 Altarac et al.
11,058,455 B2 7/2021 Cosman, Jr.
11,076,893 B2 8/2021 Altarac et al.
11,116,585 B2 9/2021 Lyons et al.
11,207,100 B2 12/2021 Donovan et al.
11,229,461 B2 1/2022 Altarac et al.
11,272,978 B2 * 3/2022 Mori ................. A61B 18/1477
11,534,236 B2 * 12/2022 Mori ..................... A61B 18/14
2002/0077683 A1 6/2002 Westlund et al.
2002/0156472 A1 10/2002 Lee et al.
2002/0165531 A1 11/2002 Goble
2003/0032951 A1 2/2003 Rittman et al.
2003/0212390 A1 11/2003 Chen et al.
2005/0065509 A1 3/2005 Coldwell et al.
2005/0277918 A1 12/2005 Shah et al.
2006/0052850 A1 3/2006 Darmos et al.
2007/0032835 A1 2/2007 Rittman
2008/0195152 A1 8/2008 Altarac et al.
2008/0200972 A1 * 8/2008 Rittman ............... A61N 1/0551 607/117
2008/0262490 A1 10/2008 Williams
2009/0138046 A1 5/2009 Altarac et al.
2010/0114093 A1 5/2010 Mahapatra et al.
2010/0222747 A1 9/2010 Wenchell et al.
2010/0249750 A1 9/2010 Racz et al.
2011/0028836 A1 2/2011 Ranpura et al.
2011/0288540 A1 11/2011 Wright et al.
2011/0301578 A1 12/2011 Muniz-Medina et al.
2012/0203064 A1 8/2012 Wynberg
2012/0215218 A1 8/2012 Lipani
2013/0345699 A1 12/2013 Brannan et al.
2014/0066917 A1 3/2014 Cosman, Jr. et al.
2014/0081260 A1 3/2014 Cosman, Jr. et al.
2014/0121656 A1 5/2014 McKay
2014/0121658 A1 5/2014 Cosman, Jr. et al.
2014/0236144 A1 8/2014 Krueger et al.
2014/0276800 A1 9/2014 Batchelor et al.

(56) References Cited

U.S. PATENT DOCUMENTS

2015/0182234 A1 7/2015 Mahoney et al.
2015/0297246 A1* 10/2015 Patel .................. A61B 17/8805 606/79
2015/0297282 A1 10/2015 Cadouri
2015/0305799 A1 10/2015 Trieu
2016/0206362 A1 7/2016 Mehta et al.
2016/0242822 A1 8/2016 Altarac et al.
2016/0278791 A1 9/2016 Pellegrino et al.
2016/0310211 A1 10/2016 Long
2017/0004951 A1 1/2017 Weisz et al.
2017/0049503 A1 2/2017 Cosman et al.
2017/0049514 A1 2/2017 Cosman
2018/0042664 A1 2/2018 Juergens
2018/0161086 A1 6/2018 Davalos et al.
2018/0318061 A1 11/2018 Clarke et al.
2019/0110833 A1 4/2019 Pellegrino et al.
2019/0117970 A1 4/2019 Schmidt et al.
2019/0201057 A1 7/2019 Altarac et al.
2019/0223948 A1 7/2019 Stewart et al.
2019/0239924 A1* 8/2019 Urbanski .............. A61M 5/007
2019/0239941 A1 8/2019 Schorr et al.
2020/0038091 A1 2/2020 Cao et al.
2020/0038096 A1 2/2020 Schepis et al.
2020/0139144 A1 5/2020 Cosman et al.
2020/0146744 A1 5/2020 Defosset et al.
2020/0205892 A1 7/2020 Viswanathan et al.
2020/0281646 A1 9/2020 Pellegrino et al.
2020/0330153 A1 10/2020 Cosman, Jr. et al.
2020/0367871 A1 11/2020 Van Voven et al.
2020/0383707 A1 12/2020 Kidman et al.
2020/0390496 A1 12/2020 Houden et al.
2021/0038298 A1 2/2021 Scott et al.
2021/0100592 A1 4/2021 Seifert et al.
2021/0121224 A1 4/2021 Ranpura et al.
2021/0236191 A1 8/2021 Wang et al.
2021/0322063 A1 10/2021 Altarac et al.
2021/0369394 A1 12/2021 Braido et al.
2021/0393315 A1 12/2021 McGregor et al.
2022/0061894 A1 3/2022 Altarac et al.
2022/0202484 A1 6/2022 Wang et al.
2022/0202485 A1 6/2022 Marusich et al.
2022/0218411 A1 7/2022 Druma et al.
2022/0226039 A1 7/2022 Wang
2022/0323147 A1 10/2022 Hata et al.
2022/0401085 A1 12/2022 Cosman, Jr.
2024/0108361 A1 4/2024 Johnson et al.
2024/0108394 A1 4/2024 Bates et al.
2024/0245445 A1 7/2024 Bates
2024/0245449 A1 7/2024 Bates
2024/0277384 A1 8/2024 Malinowski
2024/0423687 A1 12/2024 Johnson et al.
2024/0423701 A1 12/2024 Johnson et al.

FOREIGN PATENT DOCUMENTS

WO 00/59394 10/2000
WO 2007121143 10/2007
WO 2014130031 8/2014
WO WO2022011115 1/2022

OTHER PUBLICATIONS

Invitation to Pay Additional Fees and, Where Applicable, Protest Fee for PCT Application No. PCT/US2023/033835 mailed Jan. 3, 2024.
Hemostasis Vales—Qosina—URL: hllps://www.qosina.com/vascular-access-hemostasis-valves 9 pages—retrieved Nov. 13, 2019.
*Coolief* Cooled Radio Frequency Kit—Instructions for Use Halyard—dated Feb. 9, 2017—8 pages.
Cobra R-F™—Epimed—URL: https://www.epimed.com/products/cobra-r-f/—retrieved Jan. 27, 2021.
Hyso et al., "Epimed Launches "Cobra" R-F™ Dual Use Radiofrequency Cannula" Cision—PR Web—Jan. 17, 2019 3 pages.
"Venom cannula and electrode system"—Stryker—retrieved Sep. 8, 2020 URL: https://www.stryker.com/us/en/interventional-spine/products/venom-cannula-and-electrode-system.html.
"RF Trident™ Cannulae" Diros Technology Inc. Nov. 11, 2017 URL: https://web.archive.org/web/20171117054945/https://dirostech.com/product-details/rf-tridenttrident-hybrid-cannulae/.
Cedeno et al., "Comparisons of Lesion vols. and Shapes Produced by a Radiofrequency System with a Cooled, a Protruding, or a Monopolar Probe" Pain Physician 2017; 20:E915-E922 • ISSN 2150-1149.
Correspondence from Department of Health and Human Services to George Darmos at Diros Technology, Inc.—dated Jul. 30, 2015—11 pages.
Correspondence from Department of Health and Human Services to Christina McKee—dated Mar. 28, 2013; 7 pages.
Cosman et al. "Theoretical Aspects of Radiofrequency Lesions in the Dorsal Root Entry Zone," Neurosurgery, vol. 15, No. 6, p. 945-950 (1984).
U.S. Appl. No. 18/373,586, filed Sep. 27, 2023.
Rhame EE, Levey KA, Gharibo CG. Successful treatment of refractory pudendal neuralgia with pulsed radiofrequency. Pain Physician. May-Jun. 2009;12(3):633-8. PMID: 19461829.
Todorov L. Pulsed radiofrequency of the sural nerve for the treatment of chronic ankle pain. Pain Physician. May-Jun. 2011;14(3):301-4. PMID: 21587334.

* cited by examiner 104
114
148
142
113
152
146
140
150
112

113
150
112
152
154
140

113
150
112
152
154
140

160
162

160
164
162

104
114
166
113
167
160
150
112

RF ABLATION SYSTEMS WITH A BIPOLAR RF ELECTRODE AND METHODS FOR MAKING AND USING

CROSS-REFERENCE TO RELATED APPLICATIONS

This application claims the benefit under 35 U.S.C. § 119(e) of U.S. Provisional Patent Application Ser. No. 63/413,133, filed Oct. 4, 2022, which is incorporated herein by reference.

FIELD

The present disclosure is directed to the area of radiofrequency (RF) ablation systems and methods of making and using the systems. The present disclosure is also directed to RF ablation systems and methods that include a bipolar RF electrode, as well as methods of making and using the same.

BACKGROUND

Radiofrequency (RF) generators and electrodes can be used for pain relief or functional modification. Radiofrequency ablation (RFA) is a safe, proven means of interrupting pain signals, such as those coming from irritated facet joints in the spine, genicular nerves in the knee, and femoral and obturator nerves in the hip. Radiofrequency current is used to heat up a small volume of nerve tissue, thereby interrupting pain signals from that specific area. Radiofrequency ablation is designed to provide long-lasting pain relief.

For example, an RF electrode can be positioned near target tissue and then used to heat the target tissue by RF power dissipation of the RF signal output in the target tissue. Temperature monitoring of the target tissue by a temperature sensor in the electrode may be used to control the process.

BRIEF SUMMARY

In one aspect, a RF ablation electrode includes an electrode shaft; a metal tube forming at least a portion of the electrode shaft and including a proximal portion and a distal portion, wherein at least the distal portion of the metal tube includes a plurality of cuts to facilitate bending of the distal portion, wherein at least part of the distal portion of the metal tube includes a first electrode; a spacer disposed distally from the first electrode; a second electrode disposed distally from the spacer; a connector; and at least two conductors electrically coupled to the connector with different conductors of the at least two conductors electrically coupled to the first electrode and the second electrode, respectively.

In at least some aspects, the plurality of cuts is arranged as an interrupted spiral pattern. In at least some aspects, the RF ablation electrode further includes a non-conductive jacket disposed over at least the proximal portion of the metal tube but not disposed over the first electrode. In at least some aspects, the plurality of conductors includes a first conductor that is electrically attached to the proximal portion of the metal tube. In at least some aspects, the proximal portion of the metal tube does not include any of the cuts. In at least some aspects, the second electrode is a tip electrode. In at least some aspects, the spacer, first electrode, or second electrode includes a radiopaque marker.

In another aspect, a RF ablation electrode includes an electrode shaft including a proximal portion, a distal portion, and a multi-lumen tube extending along at least part of the proximal portion of the electrode shaft, the multi-lumen tube defining a plurality of conductor lumens extending along the multi-lumen tube; a first electrode disposed along, or coupled to, the distal portion of the electrode shaft; a spacer disposed distally from the first electrode; a second electrode disposed distally from the spacer; a connector; and at least two conductors electrically coupled to the connector with different conductors of the at least two conductors electrically coupled to the first electrode and the second electrode, respectively, wherein at least a portion of at least one of the at least two conductors extends along at least one of the conductor lumens of the multi-lumen tube.

In at least some aspects, the multi-lumen tube has exactly three or four of the conductor lumens. In at least some aspects, the multi-lumen tube further includes a stylet lumen that is different in size from the conductor lumens. In at least some aspects, the multi-lumen tube is made of a higher durometer material than a material forming a portion of the electrode shaft adjacent the first electrode. In at least some aspects, the second electrode is a tip or ring electrode.

A further aspect is a RF ablation system that includes any of the RF ablation electrodes described above and an RF generator coupled, or coupleable, to the RF ablation electrode.

In yet another aspect, a RF ablation system includes a bipolar RF electrode including an electrode shaft, a first electrode and a second electrode disposed along a distal portion of the electrode shaft, a connector, a first conductor electrically coupled to the first electrode and the connector, and a second conductor electrically coupled to the second electrode and the connector; and an adapter including an electrode connector configured to connect to the connector of the bipolar RF electrode, first and second port connectors configured to individually connect to different ports of a RF generator, a first adapter conductor configured to electrically couple the electrode connector to the first port connector, and a second adapter conductor configured to electrically couple the electrode connector to the second port connector, wherein, when the electrode connector of the adapter is coupled to the connector of the bipolar RF electrode, the first conductor of the bipolar RF electrode is electrically coupled to the first adapter conductor and the second conductor of the bipolar RF electrode is electrically coupled to the second adapter conductor.

In at least some aspects, the RF ablation system further includes the RF generator including a first port configured to receive the first port connector of the adapter and a second port configured to receive the second port connector of the adapter.

In another aspect, a RF ablation system includes a RF generator including a RF source, a ground, a temperature measurement arrangement, and at least one port, wherein the RF generator defines at least three channels, wherein the RF source and ground are electrically coupled to different channels of the at least three channels and the temperature measurement arrangement is electrically coupled to two of the at least three channels; and a bipolar RF electrode including an electrode shaft, a first electrode and a second electrode disposed along a distal portion of the electrode shaft, a temperature sensor disposed along the distal portion of the electrode shaft, a connector, and at least three conductors extending along the electrode shaft and electrically coupled to the connector, wherein the first and second electrodes are electrically coupled to different conductors of the at least three conductors and the temperature sensor is coupled to two of the at least three conductors, wherein the connector of the bipolar RF electrode is configured to electrically couple to at least one of the at least one port of the RF generator so that, when coupled, the first electrode is electrically coupled to the RF source, the second electrode is electrically coupled to the ground, and the temperature sensor is electrically coupled to the temperature measurement arrangement.

In at least some aspects, the at least three channels includes a first channel, a second channel, a third channel, and a fourth channel and the at least three conductors includes a first conductor coupled to the first electrode, a second conductor coupled to the second electrode, and third and fourth conductors coupled to the temperature sensor, wherein, when the connector of the bipolar RF electrode is electrically coupled to the at least one port of the RF generator, the first conductor couples the first electrode to the first channel and the RF source, the second conductor couples the second electrode to the second channel and the ground, and the third and fourth conductors couple the temperature sensor to the third and fourth channels, respectively, and the temperature measurement arrangement.

In at least some aspects, the at least three channels includes a first channel, a second channel, and a third channel and the at least three conductors includes a first conductor coupled to the first electrode, a second conductor coupled to the second electrode, and a third conductor coupled to the temperature sensor, wherein the temperature sensor is also coupled to either the first or second conductor, wherein, when the connector of the bipolar RF electrode is electrically coupled to the at least one port of the RF generator, the first conductor couples the first electrode to the first channel and the RF source, the second conductor couples the second electrode to the second channel and the ground, and the third conductor, as well as either the first or second conductor, couples the temperature sensor to the third channel, as well as either the first or second channel, respectively, and the temperature measurement arrangement. In at least some aspects, the RF generator further includes a RF filter coupled between either the first or second channel and the temperature measurement arrangement to filter out signals from the RF source.

In at least some aspects, any of the RF ablation electrodes described above can be used in any of the RF ablation systems described above.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of radiofrequency (RF) ablation systems and methods of making and using the systems. The present disclosure is also directed to RF ablation systems and methods that include a bipolar RF electrode, as well as methods of making and using the same.

Many conventional RF generators for pain management support monopolar electrodes with one conductor and a temperature measurement device, such as a thermocouple. The return path is provided by a ground pad that is attached to the patient's skin. Some RF generators for pain management also support bipolar ablation in which the conductive tips of two or more separate monopolar electrodes are placed near each other. One electrode supplies power while the other electrode acts as a return. Each electrode requires one channel on the RF generator.

Figures 1, 2:
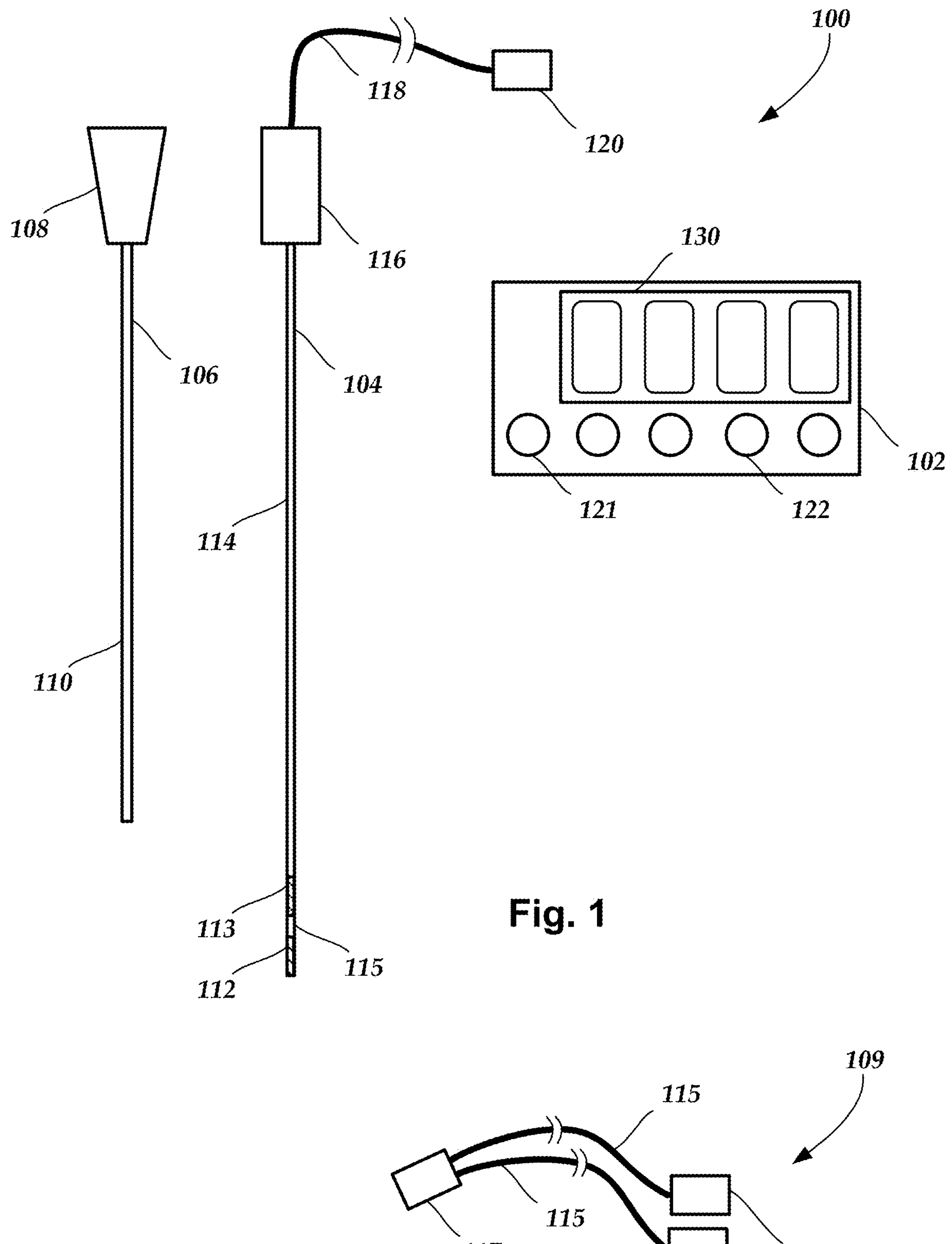
FIG. 1 is a schematic side view of components of one embodiment of a RF ablation system with a bipolar RF electrode.
FIG. 2 is a schematic side view of components of one embodiment of an adapter for coupling a bipolar RF electrode to a RF generator.

As described herein, a RF ablation system can include a bipolar electrode (i.e., a component with two electrodes on the same shaft), instead of two or more monopolar electrodes. In at least some embodiments, the RF generator that was previously coupled to monopolar electrodes can be used or adapted for use with a bipolar electrode. FIG. 1 illustrates one embodiment of a RF ablation system 100 that includes a RF generator 102, a bipolar RF electrode 104, and a cannula 106. It should be appreciated that a RF electrode may be a multipolar RF electrode having multiple electrodes on the same shaft. It will be recognized that some embodiments of a RF ablation system can include more or fewer components.

The cannula 106 includes a cannula hub 108 and a cannula shaft 110. The cannula shaft 110 is hollow for receiving the bipolar RF electrode 104. The bipolar RF electrode 104 includes an electrode shaft 114, a first electrode 112, a second electrode 113, an insulative material 115 (which may be part of the electrode shaft) separating the first and second electrodes, an electrode hub 116, a cable 118 that is electrically coupled to the electrode shaft 114, and a connector 120 for coupling to at least one port 122 of the RF generator 102 to energize the first electrode 112 or second electrode 113 (or both) via the cable 118 and connector 120.

The RF generator 102 can include one or more ports 122 and at least one screen 130. In at least some embodiments, each port 122 is associated with a portion of the screen 130 (or a different screen) and can receive the connector 120 from a bipolar RF electrode 104 or a connector from an adapter 109 (FIG. 2), as described below. Information such as current, voltage, impedance, status, or the like or any combination thereof can be displayed on the screen 130. In at least some embodiments, each port 122 corresponds to an independent channel. The RF generator 102 optionally includes a ground port 121.

Examples of RF generators and RF ablation systems and methods of making and using the RF generators and RF ablation systems can be found at, for example, U.S. Pat. Nos. 9,717,552; 9,956,032; 10,111,703; 10,136,937; 10,136,942; 10,136,943; 10,194,971; 10,342,606; 10,363,063; 10,588,687; 10,631,915; 10,639,098; and 10,639,101; and U.S. Patent Application Publications Nos. 2014/0066917; 2014/081260; 2014/0121658; 2021/0121224; 2021/0236191; 2022/0202484; 2022/0202485; and 2022/0226039, all of which are incorporated herein by reference in their entireties.

The bipolar RF electrode 104 has two conductors (such as conductors 135 illustrated in FIG. 3) that extend along the cable 118, optionally through the electrode shaft 114, and couple to the first and second electrodes 112, 113, respectively. One conductor is electrically coupled to one of the electrodes (for example, electrode 112) and supplies power to that electrode and the other conductor is electrically coupled to the other one of the electrodes (for example, electrode 113) and acts as a return. In at least some embodiments, the bipolar RF electrode includes an insulator 115 between the first and second electrodes 112, 113.

At least some RF generators provide a single channel at each port 122. In at least some embodiments, the bipolar RF electrode 104 uses a separate channel for each of the two electrodes 112, 113. In at least some embodiments, the RF ablation system 100 can include an adapter 109, illustrated in FIG. 2, with a connector 117*a* to connect to the connector 120 of the bipolar RF electrode 104, two cables 115 that are individually coupled through the connector 117*a* to a different one of the conductors (such as conductors 135 illustrated in FIG. 3) of the bipolar RF electrode, and two port connectors 117*b* for coupling to individual ports 122 of the RF generator 102. This permits one port 122 to energize one of the electrodes (for example, electrode 112) and another port 122 to act as a return using the other of the electrodes (for example, electrode 113.)

Figure 3:
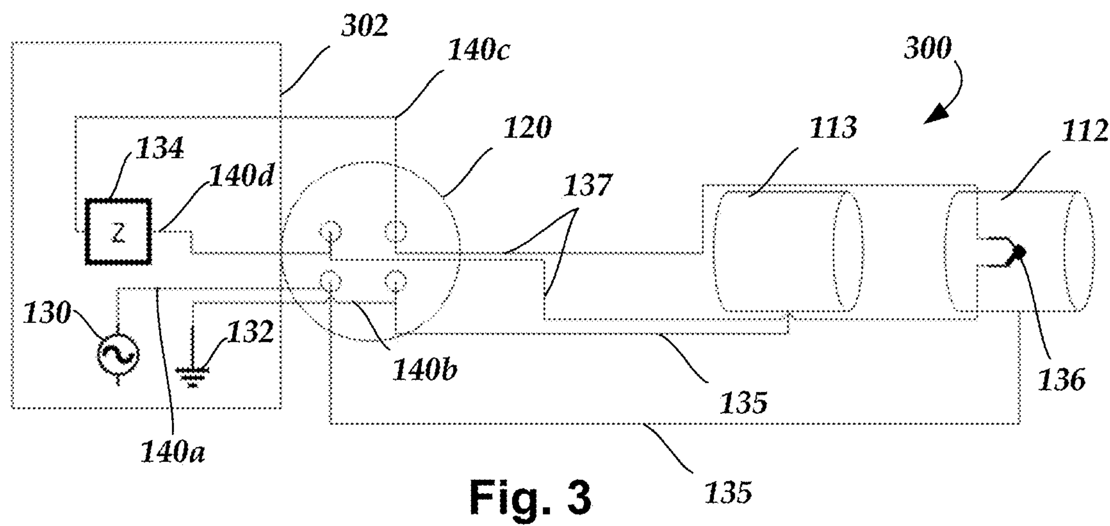
FIG. 3 is a schematic diagram of one embodiment of a RF ablation system with an RF generator and a bipolar RF electrode.

In at least some embodiments, the RF ablation system 100 can include a temperature measurement arrangement and temperature sensor (for example, a thermocouple or thermistor), which can be similar to temperature measurement arrangement 134 and temperature sensor 136 of FIG. 3 or any other temperature measurement arrangement and temperature sensor that is utilized for existing monopolar electrodes of RF ablation systems. In at least some embodiments, power or temperature calculations/measurements can be performed using one or both channels. In at least some embodiments, temperature measurements can be performed using the active electrode channel and active temperature feedback can be performed using the return electrode channel (or vice versa). In at least some embodiments, resistance or impedance can be measured for one or both channels (i.e., for one or both of electrodes 112, 113.) In at least some embodiments, if the temperature, resistance, or impedance exceeds a threshold, then a warning or error can be provided to the user through the RF generator and, optionally, the RF ablation can be halted.

FIG. 3 illustrates another embodiment of an RF ablation system 300 with the same elements as the RF ablation system 100 illustrated in FIG. 1 except as indicated herein. In RF ablation system 300, the RF generator 102 includes an RF source 130 (which is included in all RF generators described herein), a ground 132 (which is also included in all RF generators described herein), and a temperature measurement arrangement 134 (which can be included in any RF generators described herein). FIG. 3 illustrates connections (e.g., channels) between the RF generator 102 and the connector 120 of the bipolar RF electrode 104. In this embodiment, there are four different channels—one channel 140*a* coupled to the RF power source 130, one channel 140*b* coupled to the ground 132, and two channels 140*c*, 140*d* coupled to the temperature measurement arrangement 134.

FIG. 3 also illustrates the conductors 135 from the connector 120 to the first electrode 112 (e.g., the power or active electrode) and the second electrode 113 (e.g., the ground or return electrode), as well as conductors 137 to a temperature sensor 136. In this embodiment, the first electrode 112 is coupled through the connector 120 to the RF power source 130 on channel 140*a* and the second electrode 113 is coupled through the connector 120 to the ground 132 on channel 140*b*. (It will be recognized that in other embodiments, the first electrode 112 can be the return electrode and the second electrode 113 can be the active electrode with the appropriate changes to which channel the respective electrode is coupled.)

The temperature sensor 136 can be, for example, a thermistor, thermocouple, or the like or any combination thereof. In at least some embodiments, the temperature sensor 136 is disposed near the power or active electrode (e.g., electrode 112, as illustrated in FIG. 3) to obtain an accurate temperature near region where ablation energy is applied (or initially applied) to the tissue. The temperature sensor 136 is coupled through the connector 120 to the temperature measurement arrangement 134 on channels 140*c*, 140*d*.

In at least some embodiments, resistance, impedance, voltage, or the like can be measured for one or both channels 140*a*, 140*b* (i.e., for one or both of electrodes 112, 113.) In at least some embodiments, if the resistance, impedance, current, or the like exceeds a threshold, then a warning or error can be provided to the user through the RF generator and, optionally, the RF ablation can be halted.

Figure 4:
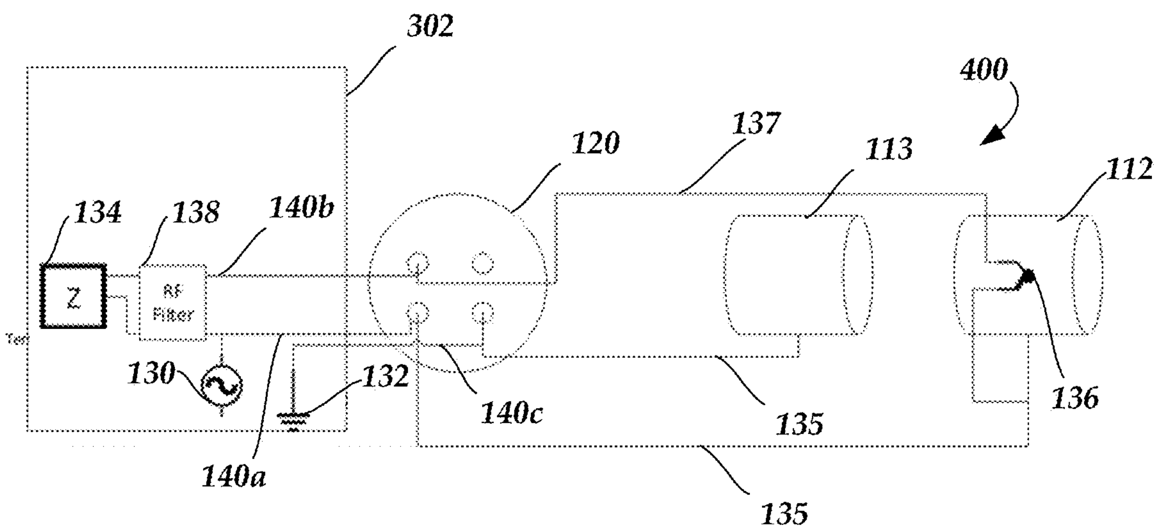
FIG. 4 is a schematic diagram of another embodiment of a RF ablation system with an RF generator and a bipolar RF electrode.

FIG. 4 illustrates yet another embodiment of an RF ablation system 400 with the same elements as the RF ablation system 100 illustrated in FIG. 1 except as indicated herein. In RF ablation system 400, the RF generator 102 includes an RF source 130, a ground 132, and a temperature measurement arrangement 134. FIG. 3 illustrates connections (e.g., channels) between the RF generator 102 and the connector 120 of the bipolar RF electrode 104. In this embodiment, there are three different channels 140*a*, 140*b*, 140*c*—one channel 140*a* coupled to the RF power source 130 and to the temperature measurement arrangement 134, another channel 140*b* coupled to the temperature measurement arrangement 134, and one channel 140*c* coupled to the ground 132.

FIG. 4 also illustrates the connections from the connector 120 to the first electrode 112 (e.g., the power or active electrode) and the second electrode 113 (e.g., the ground or return electrode), as well as connections to a temperature sensor 136. In this embodiment, the first electrode 112 is coupled through the connector 120 to the RF power source 130 on channel 140*a* and the second electrode 113 is coupled through the connector 120 to the ground 132 on channel 140*c*.

The temperature sensor 136 is coupled to the temperature measurement arrangement 134 through an RF filter 138 to remove the signal arising from the RF power source 130. Any suitable type of RF filter can be used. The temperature sensor 136 is coupled through the connector 120 to the temperature measurement arrangement 134 on channel 140*a* (which is also coupled to the active electrode 112) and channel 140*b*. It will be recognized, however, that in other embodiments, the temperature sensor 136 can be coupled through the connector 120 to the temperature measurement arrangement 134 on channel 140*b* and channel 140*c* (which is also coupled to the return electrode 113.)

In at least some embodiments, resistance, impedance, voltage, or the like can be measured for one or both channels 140*a*, 140*c* (i.e., for one or both of electrodes 112, 113.) In at least some embodiments, if the resistance, impedance, current, or the like exceeds a threshold, then a warning or error can be provided to the user through the RF generator and, optionally, the RF ablation can be halted.

The basivertebral nerve (BVN) is located at the center of vertebrae in the lower back. The BVN can be difficult to access. The ablation volume of the nerve is large enough to eliminate the pain and prevent the nerve from growing back quickly. The vertebral bodies have substantial hardness and a rough texture, which produce a mechanical stress that the electrode should withstand. In addition, the electrode must be retrieved at the end of the ablation procedure. Typically, for BVN ablation, the electrode also navigates tight turns to avoid negative outcomes like puncturing the spinal canal. In addition, the electrode experiences force applied at the hub to overcome friction and obstructions to reach the target therapy location.

Accessory tools are used by the physician to make a small, curved hole into the vertebra of the patient. The hole diameter is large enough for the electrode to be inserted and directed to the target therapy location. In at least some embodiments, the electrode has a relatively high column strength so that the tip can overcome obstructions such as bone debris.

Figure 5A:
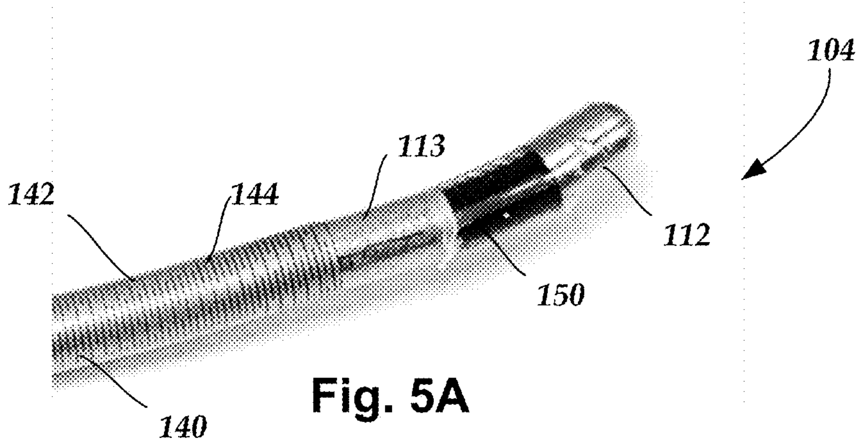
FIG. 5A is a schematic side view of a distal portion of one embodiment of a bipolar RF electrode with a metal tube forming one of the electrodes.
Figures 5B, 6A, 6B, 7A, 7B, 8:
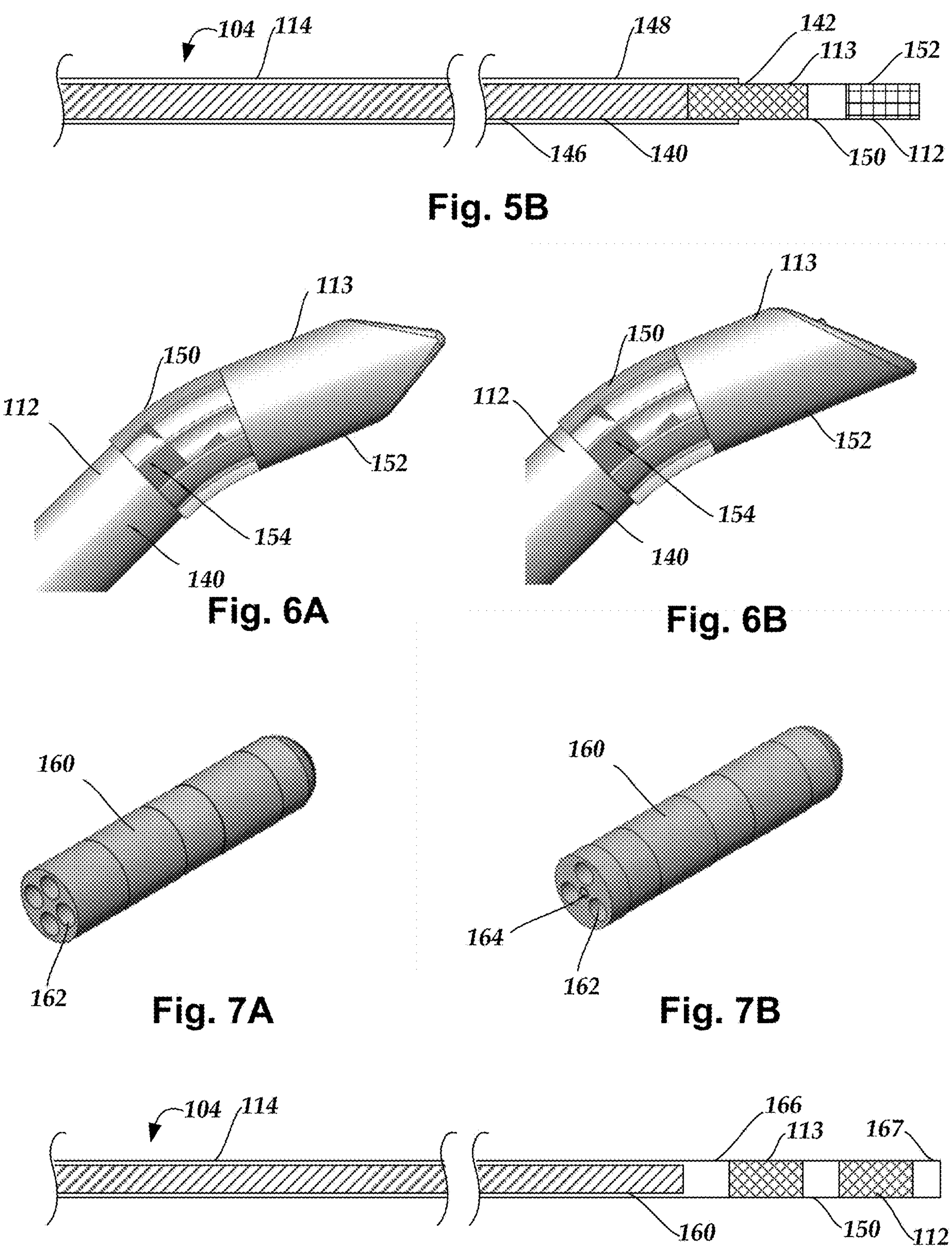
FIG. 5B is a schematic cross-sectional view of a portion of one embodiment of a bipolar RF electrode with a metal tube forming one of the electrodes.
FIG. 6A is a schematic perspective view of a distal tip portion of one embodiment of a bipolar RF electrode.
FIG. 6B is a schematic perspective view of a distal tip portion of another embodiment of a bipolar RF electrode.
FIG. 7A is a schematic perspective view of one embodiment of multi-lumen tube for use in a bipolar RF electrode.
FIG. 7B is a schematic perspective view of another embodiment of multi-lumen tube for use in a bipolar RF electrode.
FIG. 8 is a schematic cross-sectional view of a portion of one embodiment of a bipolar RF electrode with a multi-lumen tube.

In at least some embodiments, the bipolar RF electrode 104 includes a metal tube 140 with a distal portion 142 having cuts 144 (for example, laser cuts—FIG. 5A), as illustrated in FIGS. 5A and 5B, that facilitate bending of the distal portion of the tube. In at least some embodiments, the cuts 144 form an interrupted spiral pattern to provide curvature and deflection force. Other cut patterns may be used to provide ben directionality, increased torque strength, or the like. The uncut tube section 146 provides column strength and can remain straight during the insertion and ablation procedure. The distal portion 142 with the cuts 144 can bend to follow the curve tunnel within the vertebra. In at least some embodiments, at least part (or all) of the distal portion 142 of the metal tube 140 forms one of the electrodes 112, 113 of the bipolar RF electrode 104. In at least some embodiments, a non-conductive jacket 148 (made, for example, using a non-conductive polymer, such as silicone, polyester, or polyetheretherketone) covers at least part (or all) of the uncut tube section 146 and may cover part of the distal portion 142 (for example, all but the last 1 to 5 mm of the distal portion 142.) In at least some embodiments, the conductor 135 (FIG. 3) from the connector 120 (FIG. 3) is coupled to the tube 140 in, or near, the electrode hub 116 (FIG. 1) instead of extending along the length of the electrode shaft 114.

The bipolar RF electrode 104 also includes a non-conductive spacer 150 and a tip electrode 152 that is separated from the tube 140 by the non-conductive spacer. An insulated conductor extends within the electrode shaft 114 to the tip electrode 152. In at least some embodiments, the non-conductive spacer 150 is bent or is longer along one side of the spacer than along an opposing side of the spacer, as illustrated in FIGS. 6A and 6B, to facilitate bending and, at least in some embodiments, to provide lower insertion force than if the spacer were not bent. In at least some embodiments, a radio-opaque marker 154 is provided under the distal portion 142 of the tube 140 or the non-conductive spacer 150 or the tip electrode 152 or any other electrode (or any combination thereof) to facilitate visualization of the energy delivery location using fluoroscopy. The tip electrode 152 can have any suitable shape including, but not limited to, rounded (FIG. 5), chisel (FIG. 6A), bevel (FIG. 6B), or any other suitable shape.

In at least some embodiments, the electrode shaft 114 (FIG. 1) of the bipolar RF electrode 104 (FIG. 1) includes a multi-lumen tube 160, a portion of which is illustrated for two different embodiments in FIGS. 7A and 7B. In at least some embodiments, the multi-lumen tube 160 is made of a material with a relatively high durometer to provide column strength to the electrode shaft 114. In at least some embodiments, a braid or coil may be used to provide additional column strength to the electrode shaft 114. In at least some embodiments, the multi-lumen tube 160 includes two, three (FIG. 7B), four (FIG. 7A), or more conductor lumens 162 depending on the number of conductors extends along the electrode shaft 114 (see, for example, FIGS. 3 and 4 for four and three conductor arrangements.) In at least some embodiments, the conductors 135, 137 (FIG. 3) pass along the electrode shaft 114 within the conductor lumens 162 to protect the conductors during bending, implantation, and operation. In at least some embodiments, the multi-lumen shaft 160 further includes a stylet lumen 164 (FIG. 7B) for a mandrel or stylet made of metal or other rigid material to enhance the column strength of the multi-lumen shaft 160.

The distal portion 166 of the bipolar RF electrode 104 includes the first and second electrodes 112, 113, as illustrated in FIGS. 1, 5, 6A, 6B, and 8. In at least some embodiments, the first and second electrodes 112, 113 are disposed on a distal portion 166 of the electrode shaft 114 which does not include the multi-lumen tube 160, as illustrated in FIG. 8. In at least some embodiments, the distal portion 166 of the electrode shaft 114 is made of a material with substantially lower durometer than the multi-lumen shaft 160 to facilitate bending of the distal portion of the electrode shaft 114 while the multi-lumen tube 160 remains relatively straight. The first and second electrodes 112, 113 can be separated by a spacer, such as non-conductive spacer 150 described above. The distal-most electrode 113 can be a tip electrode (see, FIGS. 5, 6A, and 6B) or there can be a non-conductive tip 167 disposed distal of the distal-most electrode 113, as illustrated in FIG. 8.

It will be recognized that any combination of the features described herein for the embodiments illustrated in FIGS. 1 to 8, including, but not limited to, the adapter 109 of FIG. 2, the channel and conductor arrangements of FIGS. 3 and 4, the metal tube 140 and tip electrode 152 of FIGS. 5 to 6B, and the multi-lumen tube 160 of FIGS. 7A to 8, can be included in any embodiment of a RF ablation system or bipolar RF electrode. The length and diameter of the electrodes 112, 113, as well as the separation distance between the electrodes, can be selected or designed to provide a desirable ablation volume.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A RF ablation electrode, comprising
an electrode shaft;
a metal tube forming at least a portion of the electrode shaft and comprising a proximal portion and a distal portion, wherein at least the distal portion of the metal tube comprises a plurality of cuts to facilitate bending of the distal portion, wherein at least part of the distal portion of the metal tube forms a first electrode;
a spacer disposed distally from the first electrode;
a second electrode disposed distally from the spacer;
a connector; and
at least two conductors electrically coupled to the connector with different conductors of the at least two conductors electrically coupled to the first electrode and the second electrode, respectively.

2. The RF ablation electrode of claim 1, wherein the plurality of cuts is arranged as an interrupted spiral pattern.

3. The RF ablation electrode of claim 1, further comprising a non-conductive jacket disposed over at least the proximal portion of the metal tube but not disposed over the first electrode.

4. The RF ablation electrode of claim 1, wherein the at least two conductors comprises a first conductor that is electrically attached to the proximal portion of the metal tube.

5. The RF ablation electrode of claim 1, wherein the proximal portion of the metal tube does not comprise any of the cuts.

6. The RF ablation electrode of claim 1, wherein the second electrode is a tip electrode.

7. The RF ablation electrode of claim 1, wherein the spacer, first electrode, or second electrode comprises a radiopaque marker.

8. An RF ablation system, comprising:
the RF ablation electrode of claim 1; and
an RF generator coupled, or coupleable, to the RF ablation electrode.

9. The RF ablation electrode of claim 1, wherein the electrode shaft comprises a proximal portion, a distal portion, and a multi-lumen tube extending along at least part of the proximal portion of the electrode shaft, the multi-lumen tube defining a plurality of conductor lumens extending along the multi-lumen tube, wherein at least a portion of at least one of the at least two conductors extends along at least one of the conductor lumens of the multi-lumen tube.

10. The RF ablation electrode of claim 9, wherein the multi-lumen tube has exactly three or four of the conductor lumens.

11. The RF ablation electrode of claim 9, wherein the multi-lumen tube further comprises a stylet lumen that is different in size from the conductor lumens.

12. The RF ablation electrode of claim 9, wherein the multi-lumen tube is made of a higher durometer material than a material forming a portion of the electrode shaft adjacent the first electrode.

13. The RF ablation electrode of claim 9, wherein the second electrode is a tip or ring electrode.

14. A RF ablation system, comprising:
the RF ablation electrode of claim 9; and
an RF generator coupled, or coupleable, to the RF ablation electrode.

15. A RF ablation system, comprising
the RF ablation electrode of claim 9; and
an adapter comprising an electrode connector configured to connect to the connector of the RF ablation electrode, first and second port connectors configured to individually connect to different ports of a RF generator, a first adapter conductor configured to electrically couple the electrode connector to the first port connector, and a second adapter conductor configured to electrically couple the electrode connector to the second port connector, wherein, when the electrode connector of the adapter is coupled to the connector of the RF ablation electrode, a first one of the at least two conductors of the RF ablation electrode is electrically coupled to the first adapter conductor and a second one of the at least two conductors of the RF ablation electrode is electrically coupled to the second adapter conductor.

16. The RF ablation system of claim 15, further comprising the RF generator comprising a first port configured to receive the first port connector of the adapter and a second port configured to receive the second port connector of the adapter.

17. A RF ablation system, comprising:
a RF generator comprising a RF source, a ground, a temperature measurement arrangement, and at least one port, wherein the RF generator defines at least three channels, wherein the RF source and ground are electrically coupled to different channels of the at least three channels and the temperature measurement arrangement is electrically coupled to two of the at least three channels; and
the RF ablation electrode of claim 1, wherein the RF ablation electrodes further comprises a temperature sensor disposed along the distal portion of the electrode shaft, wherein the at least two conductors comprise at least three conductors extending along the electrode shaft and electrically coupled to the connector, wherein the first and second electrodes are electrically coupled to different conductors of the at least three conductors and the temperature sensor is coupled to two of the at least three conductors, wherein the connector is configured to electrically couple to at least one of the at least one port of the RF generator so that, when coupled, the first electrode is electrically coupled to the RF source, the second electrode is electrically coupled to the ground, and the temperature sensor is electrically coupled to the temperature measurement arrangement.

18. The RF ablation system of claim 17, wherein the at least three channels comprises a first channel, a second channel, a third channel, and a fourth channel and the at least three conductors comprises a first conductor coupled to the first electrode, a second conductor coupled to the second electrode, and third and fourth conductors coupled to the temperature sensor, wherein, when the connector is electrically coupled to the at least one port of the RF generator, the first conductor couples the first electrode to the first channel and the RF source, the second conductor couples the second electrode to the second channel and the ground, and the third and fourth conductors couple the temperature sensor to the third and fourth channels, respectively, and the temperature measurement arrangement.

19. The RF ablation system of claim 17, wherein the at least three channels comprises a first channel, a second channel, and a third channel and the at least three conductors comprises a first conductor coupled to the first electrode, a second conductor coupled to the second electrode, and a third conductor coupled to the temperature sensor, wherein the temperature sensor is also coupled to either the first or second conductor, wherein, when the connector is electrically coupled to the at least one port of the RF generator, the first conductor couples the first electrode to the first channel and the RF source, the second conductor couples the second electrode to the second channel and the ground, and the third conductor, as well as either the first or second conductor, couples the temperature sensor to the third channel, as well as either the first or second channel, respectively, and the temperature measurement arrangement.

20. The RF ablation system of claim 19, wherein the RF generator further comprises a RF filter coupled between either the first or second channel and the temperature measurement arrangement to filter out signals from the RF source.

* * * * *